US012648507B2

(12) United States Patent
Rotole et al.

(10) Patent No.: US 12,648,507 B2
(45) Date of Patent: Jun. 9, 2026

(54) CLOSED LOOP CLOSING SYSTEM CONTROL

(71) Applicant: Deere & Company, Moline, IL (US)

(72) Inventors: David V. Rotole, Bloomfield, IA (US); Cary S. Hubner, Geneseo, IL (US)

(73) Assignee: Deere & Company, Moline, IL (US)

( * ) Notice: Subject to any disclaimer, the term of this patent is extended or adjusted under 35 U.S.C. 154(b) by 577 days.

(21) Appl. No.: 18/158,008

(22) Filed: Jan. 23, 2023

(65) Prior Publication Data

US 2024/0244990 A1    Jul. 25, 2024

(51) Int. Cl.
| | |
|---|---|
| *A01B 79/02* | (2006.01) |
| *A01C 5/06* | (2006.01) |
| *G01N 33/24* | (2006.01) |
| *G06T 7/00* | (2017.01) |

(52) U.S. Cl.
CPC .............. *A01B 79/02* (2013.01); *A01C 5/068* (2013.01); *G01N 33/246* (2013.01); *G06T 7/0004* (2013.01); *A01C 5/064* (2013.01); *G01N 33/245* (2024.05); *G06T 2207/10012* (2013.01); *G06T 2207/30164* (2013.01); *G06T 2207/30188* (2013.01)

(58) Field of Classification Search
CPC ...... A01B 79/02; A01C 5/068; G01N 33/245; G01N 33/246; G06T 7/0004
See application file for complete search history.

(56) References Cited

U.S. PATENT DOCUMENTS

| | | | | |
|---|---|---|---|---|
| 8,910,582 B2 * | 12/2014 | Mariman | ............... | A01C 7/205 |
| | | | | 111/190 |
| 11,991,948 B1 * | 5/2024 | Robertson | .............. | A01C 5/066 |
| 12,102,030 B2 * | 10/2024 | Kowalchuk | .......... | A01B 63/008 |
| 2019/0239418 A1 * | 8/2019 | Smith | .................... | A01C 5/068 |
| 2019/0254223 A1 * | 8/2019 | Eichhorn | .............. | A01B 63/16 |
| 2019/0373797 A1 * | 12/2019 | Schoeny | .............. | A01C 5/068 |
| 2020/0068778 A1 * | 3/2020 | Schoeny | .............. | A01C 7/203 |
| 2020/0107488 A1 * | 4/2020 | Schoeny | .............. | A01C 5/068 |
| 2020/0404833 A1 * | 12/2020 | Stanhope | .............. | A01C 5/066 |
| 2024/0206362 A1 | 6/2024 | Stanhope et al. | | |

FOREIGN PATENT DOCUMENTS

WO      WO 2019/099748 A1      5/2019

OTHER PUBLICATIONS

Extended European Search Report and Written Opinion issued in European Patent Application No. 23217225.4 dated May 27, 2024, in 10 pages.

* cited by examiner

*Primary Examiner* — Matthew R Buck
(74) *Attorney, Agent, or Firm* — Christopher J. Volkmann; KELLY, HOLT & CHRISTENSON PLLC

(57) ABSTRACT

An agricultural machine includes a furrow opener and a furrow closing system and a controller that performs closed loop control of the furrow closing system.

19 Claims, 14 Drawing Sheets

FURROW CLOSING SYSTEM CONTROLLER 98

SOIL TYPE SENSOR 150

SOIL MOISTURE SENSOR 148

CLOSED LOOP CLOSING SYSTEM CONTROL

FIELD OF THE DESCRIPTION

The present description generally relates to planting equipment. More specifically, but not by limitation, the present description relates to a control system configured to control the closing system of an agricultural planting machine.

BACKGROUND

There are a wide variety of different types of agricultural seeding or planting machines. Such machines can include row crop planters, grain drills, air seeders or the like. These machines place seeds at a desired depth within a plurality of parallel seed trenches or furrows that are formed in the soil. Thus, some of the machines can carry one or more seed hoppers and a plurality of row units. The row units are used for opening a furrow and moving the seed from the seed hopper to the ground. The row units also use a furrow closing system to close the furrow. The row units can include a seed metering system and a seed delivery system.

The seed metering system receives the seeds in a bulk manner and divides the seeds into smaller quantities (such as a single seed, or a small number of seeds-depending on the seed size and seed type) and delivers the metered seeds to the seed delivery system. There are different types of seed metering systems and, in one example, the seed metering system uses a rotating mechanism (which may be a disc or a concave or bowl-shaped mechanism) that has seed receiving apertures, that receive the seeds from a seed pool and move the seeds from the seed pool to the seed delivery system which delivers the seeds to the ground (or to a location below the surface of the ground, such as in a trench). Other types of seed metering systems can be used as well.

There are also different types of seed delivery systems that move the seed from the seed metering system to the ground. One seed delivery system is a gravity drop system that includes a seed tube that has an inlet positioned below the seed metering system. Metered seeds from the seed metering system are dropped into the seed tube and fall (via gravitational force) through the seed tube into the seed trench. Other types of seed delivery systems are assistive systems, in that they do not simply rely on gravity to move the seed from the metering mechanism into the ground. Instead, such systems actively capture the seeds from the seed meter and physically move the seeds from the meter to a lower opening, where the seeds exit into the ground or trench.

In these types of planting machines, the row units have a controllable downforce actuator that is actuated to exert downforce on the row unit. The row unit includes controllable gage wheels that are configured to control the depth of the furrow and thus the depth of the planted seed.

The discussion above is merely provided for general background information and is not intended to be used as an aid in determining the scope of the claimed subject matter.

SUMMARY

An agricultural machine includes a furrow opener and a furrow closing system and a controller that performs closed loop control of the furrow closing system.

This Summary is provided to introduce a selection of concepts in a simplified form that is further described below in the Detailed Description. This Summary is not intended to identify key features or essential features of the claimed subject matter, nor is it intended to be used as an aid in determining the scope of the claimed subject matter. The claimed subject matter is not limited to implementations that solve any or all disadvantages noted in the background.

DETAILED DESCRIPTION

Figure 1:
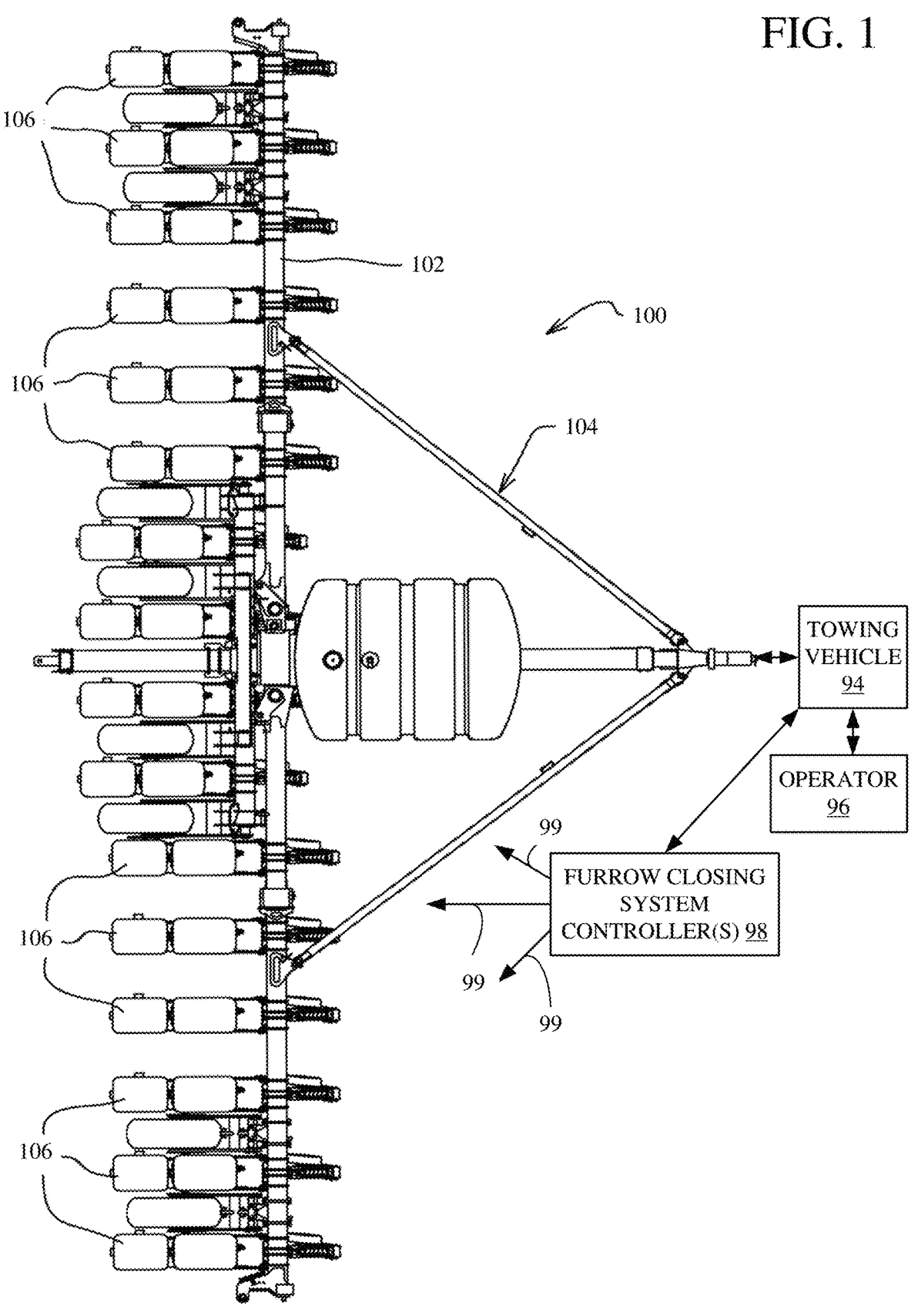
FIG. 1 shows one example of a top view of an agricultural machine.

The present description generally relates to planting equipment. An example agricultural planting machine includes a row unit with a seeding system that meters seeds from a source and delivers the metered seeds to a furrow or trench formed in the ground and then uses a closing system to close the furrow.

The row units also have a downforce actuator that is used to apply downforce to the row unit in order to assist in controlling the depth of the furrow or trench opened by the row unit. The row unit has gage wheels that are used to limit the depth of penetration of the furrow opener. The closing system has an actuator that can be controlled by a furrow closing system controller to exert downforce and/or upforce on the closing system. Also, the closing system can be configured with a mutating or configurable closing system and/or a secondary closing system. The configuration and/or secondary closing system can also be controlled by the furrow closing system controller.

The closure of the seed furrow is an important part of the planting operation. A proper closing with good seed-to-soil contact and seed-to-moisture contact provides for consistent seed germination and emergence. Different types of closing wheels (or other closing systems) may have different types of soil-engaging surfaces and may work better than other types of closing systems in different types of conditions. For example, a spiked closing wheel is sometimes desirable in hard-packed soil or in clay conditions. In softer, drier conditions, a smooth closing wheel may operate better.

The conditions of a field can vary rapidly, as the planting machine moves through the field. For instance, in hilly areas, even if a field is generally dry, the soil moisture can change very quickly and frequently as the planting machine goes through lower, wetter areas within the field.

These types of changing conditions can mean that the furrow closing system should be controlled in different ways to accommodate the different conditions. For instance, it may be that the closing wheel downforce should be adjusted to achieve better closing performance under certain conditions within the field. Similarly, it may be that the configuration of the closing wheel should be modified to accommodate the different conditions. This can be very cumbersome, as it may mean that the operator of a towing vehicle (that is towing the planting machine) must stop the vehicle, exit the operator compartment, make adjustments (to the closing wheel downforce or the closing wheel configuration), and then re-enter the operator compartment to resume the planting operation. Even in systems where the downforce on the closing wheel can be controlled, there is often no closed loop type of control system that controls the downforce or upforce on the closing wheel, or the configuration of the closing wheel, based upon a sensed variable.

The present system thus includes a furrow closing system controller that performs closed loop feedback in controlling a furrow closing system. In one example, the furrow closing system controller receive an input indicative of a sensed variable, such as soil moisture, soil type, etc. and generates a control signal to adjust the furrow closing system down/upforce based upon the sensor inputs. In another example, the furrow closing system controller receives an input indicative of furrow closing quality (such as an optical input generated by an image capture device that shows whether the furrow is properly closed) and controls the furrow closing system based upon the sensed furrow closing quality. In yet another example, the furrow closing system includes a primary closing system and a secondary closing system, and the furrow closing system controller controls one or both of the primary and secondary closing systems in a closed loop fashion. The furrow closing system can also have a mutateable or adjustable closing system, such as a closing wheel that can be configured between a smooth closing wheel and a spiked or otherwise non-smooth closing wheel. In such an example, the furrow closing system controller can control the configuration of the furrow closing system.

FIG. 1 is a top view of one example of an agricultural machine 100. Agricultural machine 100 includes a towed implement that illustratively includes a toolbar 102 that is part of a frame 104. FIG. 1 also shows that a plurality of row units 106 are mounted to the toolbar. Agricultural machine 100 can be towed behind another machine, such as a tractor (the towing vehicle 94), that may be operated by an operator 96. The row units 106 open a furrow, deliver seed to the furrow, and close the furrow. A furrow closing system controller 98 generates control signals (indicated by arrows 99) to control a furrow closing system on the row units 106. There can be a single furrow closing system controller 98 that controls the furrow closing systems on row units 106, individually or in sets. There can also be a plurality of furrow closing systems controllers 98. One or more furrow closing system controllers 98 can be disposed on each row unit 106, or on towing vehicle 94, or disbursed at different locations.

Figure 2A:
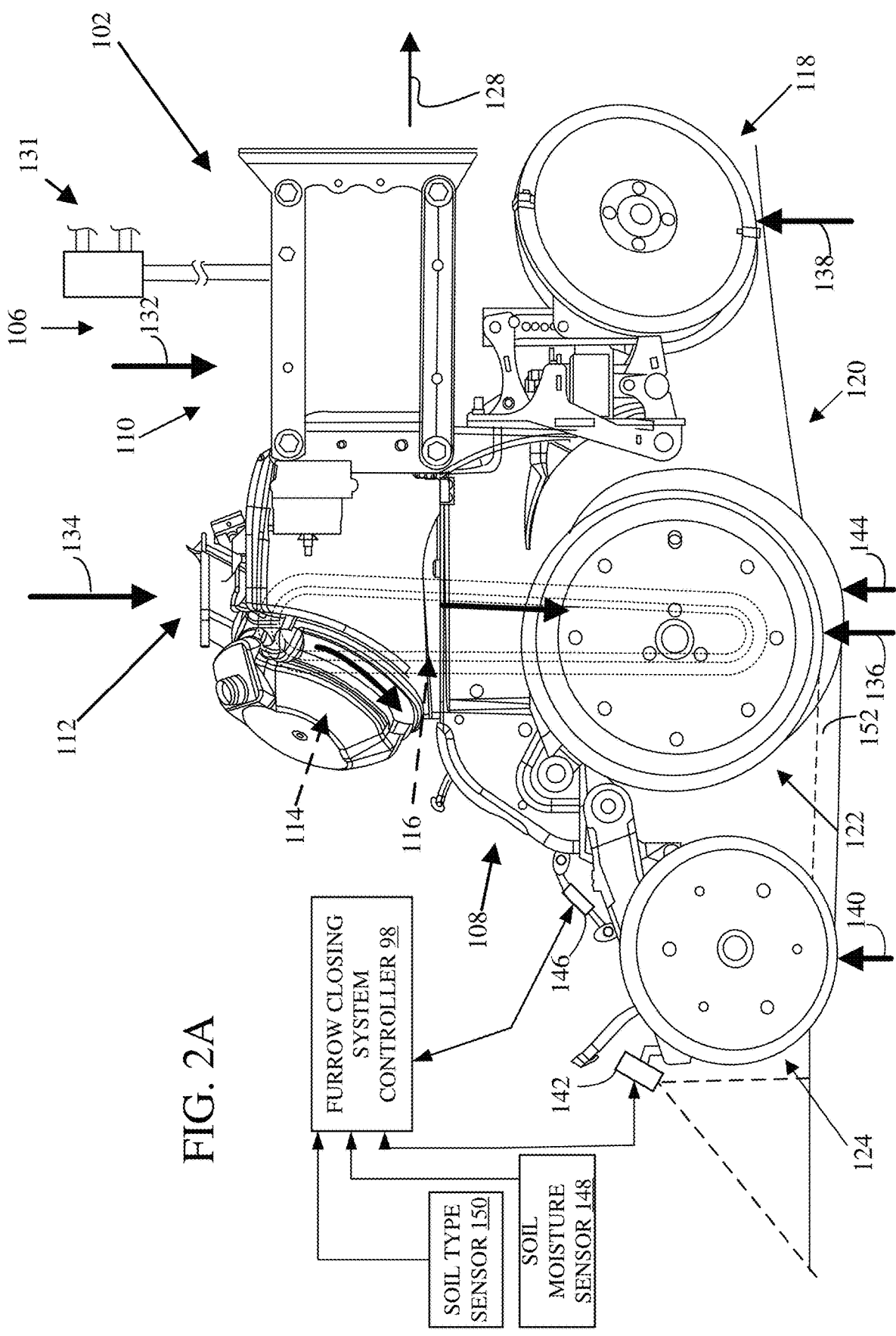
FIG. 2A shows one example of a side view of a row unit of an agricultural machine.

FIG. 2 is a side view showing one example of a row unit 106 (or a portion of row unit 106) in more detail. FIG. 2 shows that each row unit 106 illustratively has a frame 108.

Frame 108 is illustratively connected to toolbar 102 by a linkage shown generally at 110. Linkage 110 is illustratively mounted to toolbar 102 so that linkage 110 can move upwardly and downwardly (relative to toolbar 102).

Row unit 106 also illustratively has a seed hopper 112 that receives or stores seed. The seed is provided from hopper 112 to a seed metering system 114 that meters the seed and provides the metered seed to a seed delivery system 116 that delivers the seed from the seed metering system 114 to the furrow or trench generated by the row unit. In one example, seed metering system 114 uses a rotatable member, such as a disc or concave-shaped rotating member, and an air pressure differential to retain seed on the disc and move the seed from a seed pool of seeds (provided through hopper 112) to the seed delivery system 116. Other types of meters can be used as well such as a more centralized seed meter that meters seed to multiple row units 106. Row unit 106 can also include an additional hopper that can be used to provide additional material, such as fertilizer or another chemical or mechanical.

Row unit 106 includes furrow opener 120 and a set of gage wheels 122. In operation, row unit 106 moves generally in a direction indicated by arrow 128. Furrow opener 120 has blades or disks that open a furrow on the soil. Gage wheels 122 control a depth of the furrow, and seed is metered by seed metering system 114 and delivered to the furrow by seed delivery system 116. A downforce/upforce generator (or actuator) 131 can also be provided to controllably exert downforce and/or upforce to keep the row unit 106 in desired engagement with the soil. Downforce/upforce generator 131 can be a single acting actuator (such as where only downforce is applied), multiple actuators (e.g., one for downforce and one for upforce), or a double acting actuator, such as a double acting hydraulic cylinder, a pneumatic actuator, or another actuator that transfers downforce (and/or upforce) from toolbar 102 to row unit 106.

Therefore, in one example, the downforce acting on row unit 106 includes the row unit downforce (or upforce) generated by downforce/upforce actuator 131 represented by arrow 132 in FIG. 2. The downforce acting on row unit 106 also includes the self-weight of row unit 106 and the components of row unit 106 as represented by arrow 134 in FIG. 2. The downforces 132 and 134 are countered by the force that the ground exerts on the blades on furrow opener 120 that are opening the furrow in the soil, as represented by arrow 144 in FIG. 2. The downforces 132 and 134 are also countered by the force that the ground exerts on the gage wheels 122 (the gage wheel reaction force) indicated by arrow 136 in FIG. 2.

FIG. 2 also shows that row unit 106 includes a furrow closing system that has closing wheels 124. Closing wheels 124 close the furrow, that is opened by furrow opener 120, over the seed. In the example shown in FIG. 2, the downforce exerted on row unit 106 is also countered by the upwardly directed force imparted on closing wheels 124, as represented by arrow 140 in FIG. 2. In one example, a closing system down/up force actuator 146 may be a double acting or a single acting actuator that can apply force (one or both of downforce and upforce) to closing wheel 124 from frame 108. A soil moisture sensor 148 can sense soil moisture and provide a sensor signal indicative of or responsive to soil moisture to controller 98. Sensor 148 can be a conductive sensor or another sensor. A soil type sensor 150 senses soil type and provides a sensor signal indicative of or responsive to soil type to controller 98. Sensor 150 can be an optical sensor, a ph sensor, or another sensor. In one example, a sensor that senses a variable indicative of the furrow closing performance of the furrow closing system, provides a signal to controller 98. For example, an image capture device 142, such as a mono or stereo camera, can be mounted to row unit 106 to capture an image behind row unit 106, in the direction of travel, to obtain an image (static or video) of the field after furrow closing wheel 124 has passed over the ground. The image generated by image capture device 142 can be processed to obtain a performance indicator indicative of how well the furrow closing system performed in closing the furrow. The image and/or performance indicator and/or sensor signals from sensors 148 and/or 150 can be provided to furrow closing system controller 98 for use in controlling the furrow closing system (e.g., closing wheel 124).

FIG. 2 also shows that row unit 106 includes a row cleaner 118. Row cleaner 118 generally cleans the row ahead of the opener 120 to remove plant, dirt clumps, debris and other items from the previous growing season. Therefore, the downforce on row unit 106 is also countered by an upwardly directed force that the ground exerts on row cleaner 118, as indicated by arrow 138. Second dictation In operation, towing vehicle 94 tows row unit 106 generally in the direction indicated by arrow 128. Row cleaner 108 can clean residue, dirt clumps, and other material from the path of disc opener 120. Opener 120 opens a furrow 152 in the soil over which row unit 106 is traveling. Seed is delivered to hopper 112 and metered by metering system 114 and seed delivery system 116 and delivers the seed to furrow 152. Downforce/upforce can be applied on row unit 106 by downforce/upforce actuator 131. Gauge wheels 122 set the depth of furrow 152 by regulating the depth by which opener 120 penetrates the soil. Closing system (e.g., closing wheels 124) close the furrow 152. Furrow closing system controller 98 can receive one or more sensor signals and control furrow closing system 124 in a closed loop manner. For instance, based upon the soil moisture signal received from soil moisture sensor 148, controller 98 can control actuator 146 to apply upforce or downforce to closing wheels 124. Based upon the image captured from image capture device 142, controller 98 can also control the furrow closing system (e.g., closing wheels 124 and/or actuator 146). Further, based upon the soil type indicated by the signal generated from soil type sensor 150, controller 98 can control the furrow closing system. Some examples of the operation of furrow closing system controller 98 and row unit 106 are described in greater detail elsewhere herein.

Figure 2B:
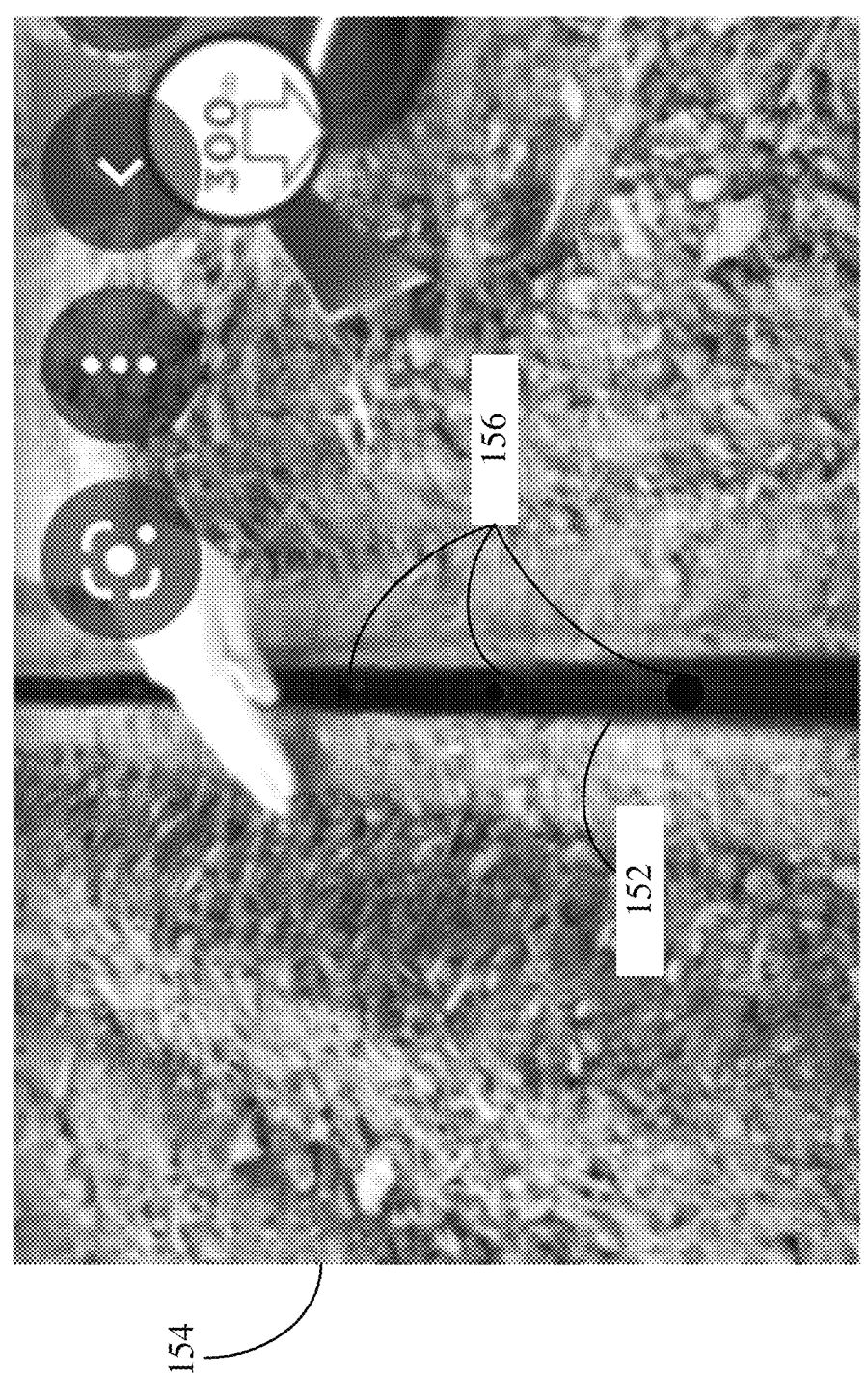
FIG. 2B shows an image of a furrow captured by an optical sensor.

FIG. 2B shows one example of an image 154 that can be generated by image capture device 142. In the example shown in FIG. 2B, image 154 is generated by a stereo camera which captures an image of furrow 152, after closing wheels 124 have traveled over it. It can be seen in the example shown in FIG. 2B that furrow 152 is still open so that the seeds 156 that have been placed in the furrow are not adequately covered. This can be caused for a variety of different reasons, such as soil moisture, soil type, the downforce or upforce exerted by actuator 146, the type of closing wheels 124 being used, among other things. The image 154 (and other images captured by image capture device 142) can be analyzed using an image processor to identify a performance metric indicative of the quality of performance of the furrow closing system (e.g., closing wheels 124 and actuator 146). Based upon the performance metric, furrow closing system controller 98 can generate control signals to control the furrow closing system (e.g., to increase or decrease the amount of force applied by actuator 146, etc.) in a closed loop fashion.

Figure 3:
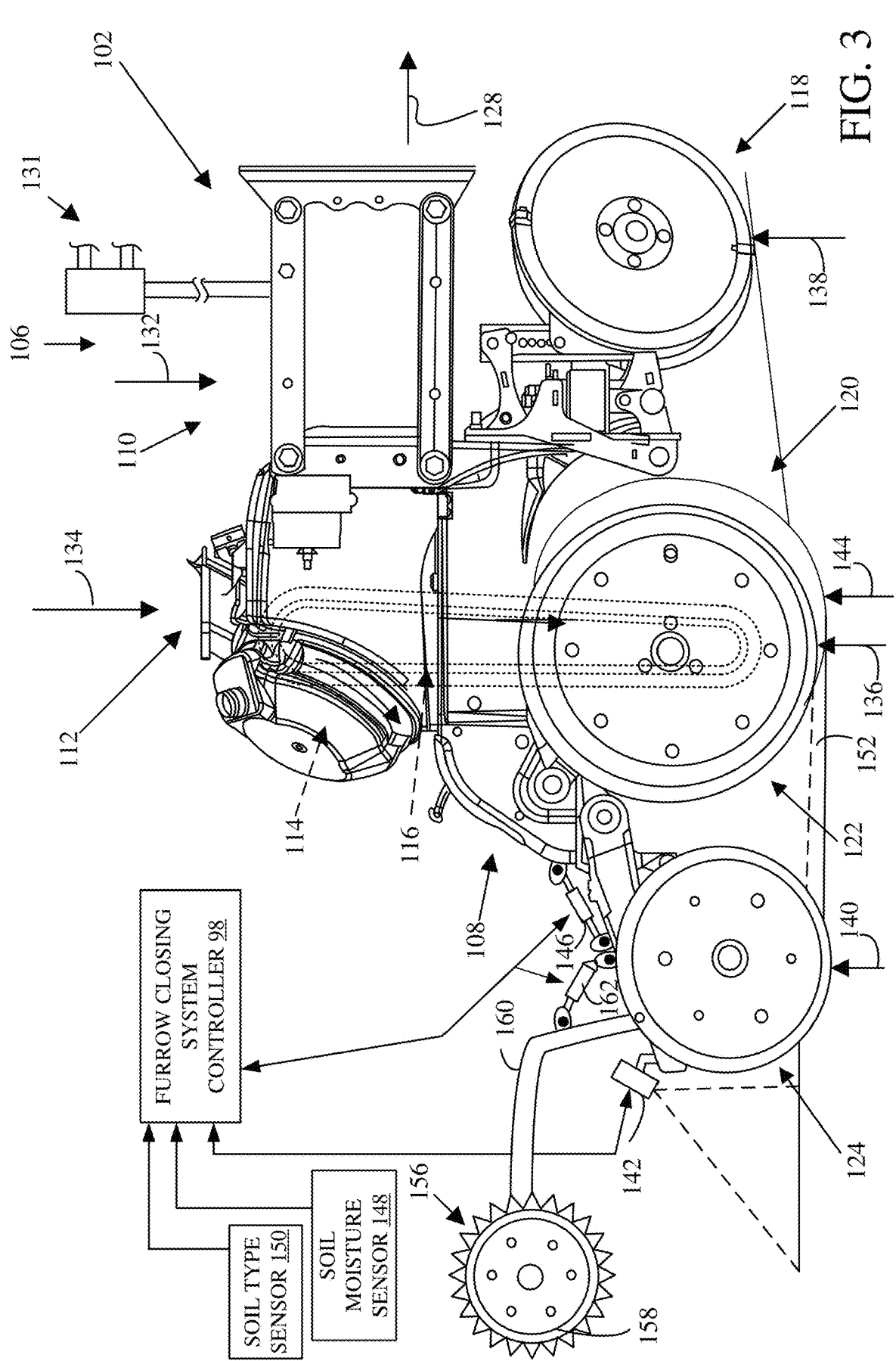
FIG. 3 shows another example of a side view of a row unit of an agricultural machine.

FIG. 3 is a side view of another example of a row unit 106. Some items are similar to those shown in FIG. 2A and they are similarly numbered. However, FIG. 3 shows that row unit 106 has a secondary furrow closing system 156. Secondary furrow closing system 156 includes one or more secondary closing wheels 158 that are pivotably mounted to frame 108 by mounting arm 160. A secondary closing actuator 162 can be a single acting actuator, or a double acting actuator, or a plurality of actuators, and is controlled by furrow closing system controller 98 to either move secondary furrow closing system 156 into engagement with the soil, or out of engagement with the soil. Actuator 162 can also be controlled to exert varying amounts of downforce or upforce on closing wheel 158. It will be noted that closing wheel 158 is illustrated as a spiked wheel, but it could be a smooth wheel or have a different type of soil engaging surface, or be a different type of closing system as well.

By way of example, assume that image capture device 142 has captured an image similar to that shown in FIG. 2B. An image processing system on furrow closing system controller 98 (or elsewhere) identifies that the operation of furrow closing wheels 124 is poor because furrow 152 has remained open even after furrow closing wheels 124 have attempted to close the furrow. In that case, closing system controller 98 can actuate actuator 162 to have secondary furrow closing wheels 158 engage the soil in an attempt to close furrow 152. Similarly, where the soil is hard or otherwise would benefit from the secondary closing system 156, system 156 can be controlled to engage the soil. However, where closing wheels 124 are performing adequately, then secondary furrow closing system 156 can be controlled to come out of engagement with the soil for more efficient operation.

It will be noted that the furrow closing system(s) can have a single closing wheel, a pair of closing wheels, or other configurations. Before describing the operation of furrow closing system controller 98 in more detail, a discussion of some other configurations of closing wheel 124 and/or closing wheel 158 will first be discussed.

Figures 4A, 4B:
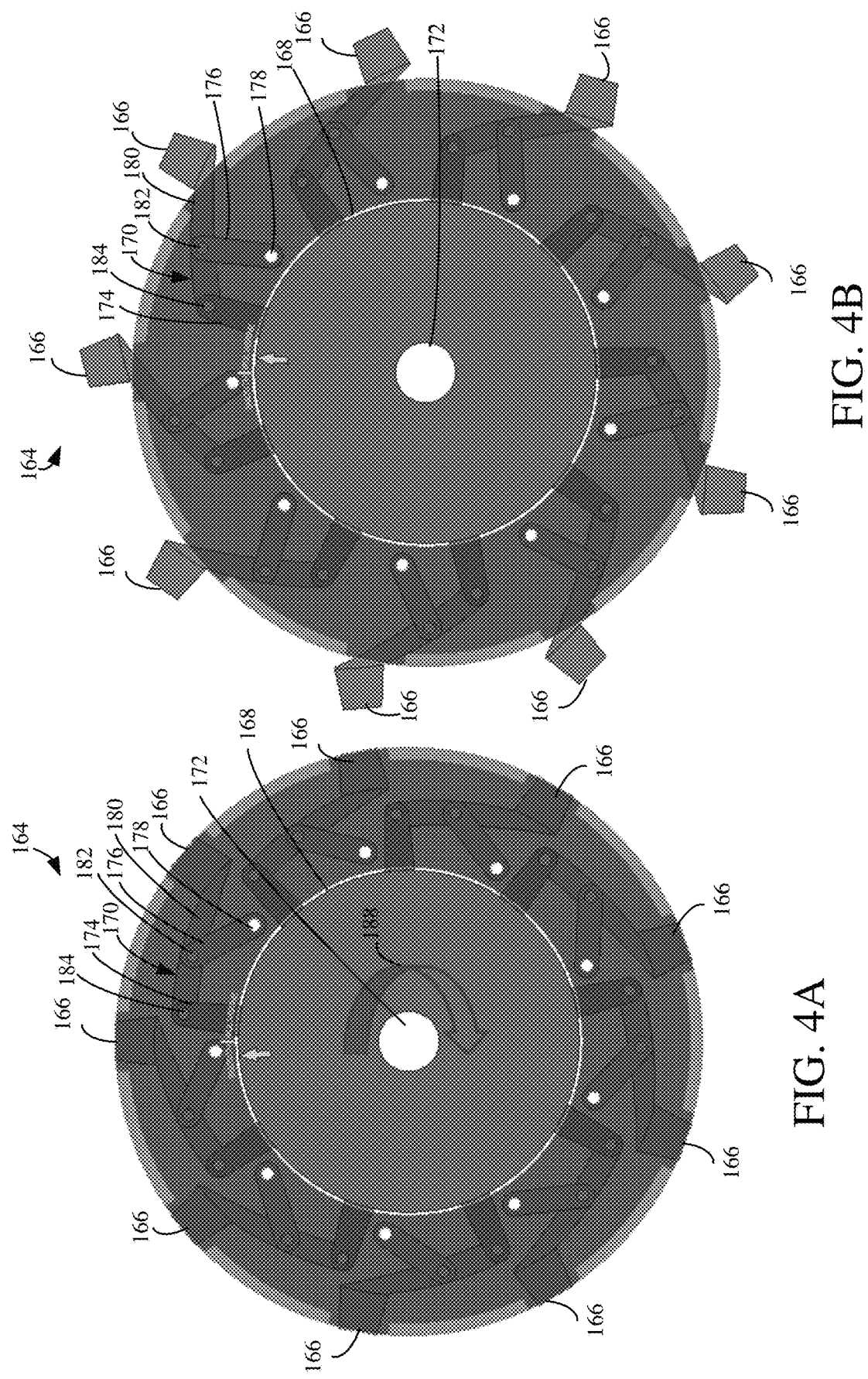
FIG. 4A and 4B show one example of a configurable closing system.

FIGS. 4A and 4B show example of a mutateable or adjustable closing wheel 164. The closing wheel 164 has a plurality of retractable spikes or studs 166. The studs 166 can be formed with different geometric shapes to perform soil engagement with varying degrees of aggressiveness. For example, if studs 166 are sharply spiked, they may engage the soil more aggressively (e.g., penetrate the soil more readily or easily with less applied downforce) than if studs 166 are more blunt. Each of the spikes or studs 166 is connected to an actuator. In the example shown in FIGS. 4A and 4B, the actuator is a rotatable hub 168 that is connected to each stud 166 by a mechanical linkage (or connection assembly) 170. In the example shown in FIGS. 4A and 4B, the mechanical linkage 170 is four bar mechanism in which hub 168 serves as one of the linkages or bars that is common to all of the mechanical linkages 170. Hub 168 is rotatable about a central axis 172 of rotation. A second bar 174 in the mechanical linkage 170 is fixedly coupled to the outer periphery of hub 168. A third bar 176 is pivotally coupled at pivot point 178 to a frame of the closing wheel 164 and is also pivotally coupled to a third bar 180 at pivot point 182. Bar 174 is also pivotally coupled to bar 180 at pivot point 184. As the hub 168 is rotated generally in the direction indicated by arrow 188, the four bar linkage rotates from the position shown in FIG. 4A (in which all studs 166 are retracted so that the soil engaging surface of the closing wheel 164 is relatively smooth) to the position shown in FIG. 4B (in which all of the studs 166 are extended to protrude outwardly from the surface of closing wheel 164) to provide a studded or spiked soil engaging surface. Hub 168 can then be rotated in a direction opposite that illustrated by arrow 188 to again retract the spikes or studs 166 either fully to partially within the surface of wheel 164. It will be appreciated that, in the example shown in FIG. 4A, the distal surface of each stud 166 can be positioned to form a part of the soil engaging surface of wheel 164 even when the studs are fully retracted. Depending on the desired aggressiveness of soil engagement, studs 166 can be moved to a fully retracted position shown in FIG. 1A, to a fully extended position shown in FIG. 4B, or to a position intermediate the positions shown in FIGS. 4A and 4B.

Figures 5A, 5B:
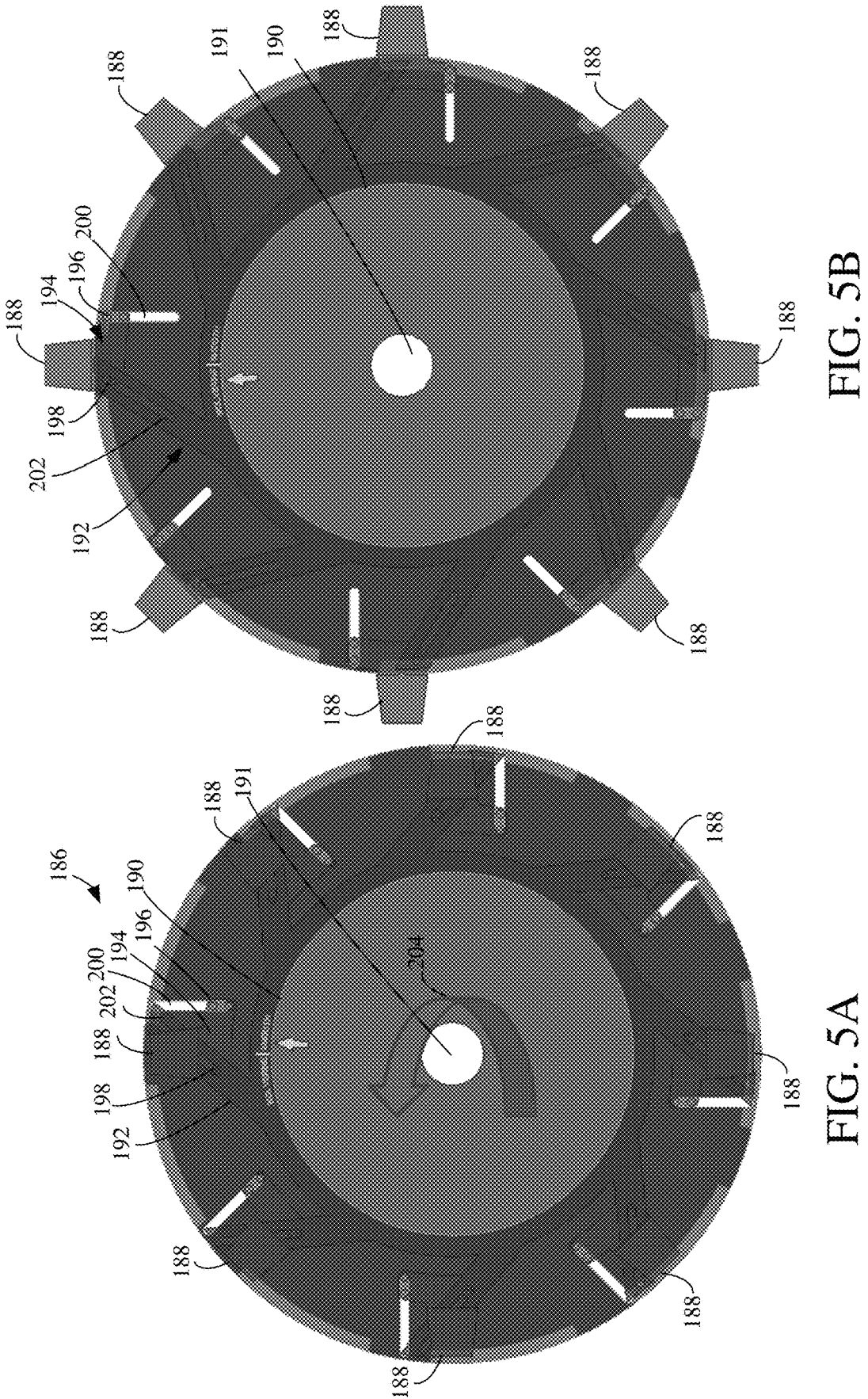
FIG. 5A and 5B show one example of a configurable closing system.

FIGS. 5A and 5B show another example of an adjustable or configurable closing wheel 186. In the example shown in FIGS. 5A and 5B, closing wheel 186 also has a plurality of studs or teeth 188 that are connected to an internal, rotatable hub 190 which rotates about an axis 191 of rotation. The teeth or studs 188 are connected to hub 190 by a dual slot connection mechanism 192. A tooth carrier 194 has pins 196 and 198 connected to travel in corresponding slots 200 and 202. As hub 190 is rotated in the direction generally indicated by arrow 204, the pins 196 and 198 move radially upwardly or outwardly relative to hub 190 to drive tooth carrier 194 in the same direction, and thus to cause teeth or studs 188 to protrude from the surface of closing wheel 186, as shown in FIG. 5B. Again, when the teeth or studs 188 are fully retracted, they can have a distal surface that forms part of the soil engaging surface of wheel 186. Also, as with the example shown in FIGS. 4A and 4B, the hub 190 can be controlled to position the teeth or studs 188 in either of the extreme positions shown in FIGS. 5A and 5B, or in an intermediate position, depending on the desired aggressiveness of soil engagement.

Figures 6A, 6B:
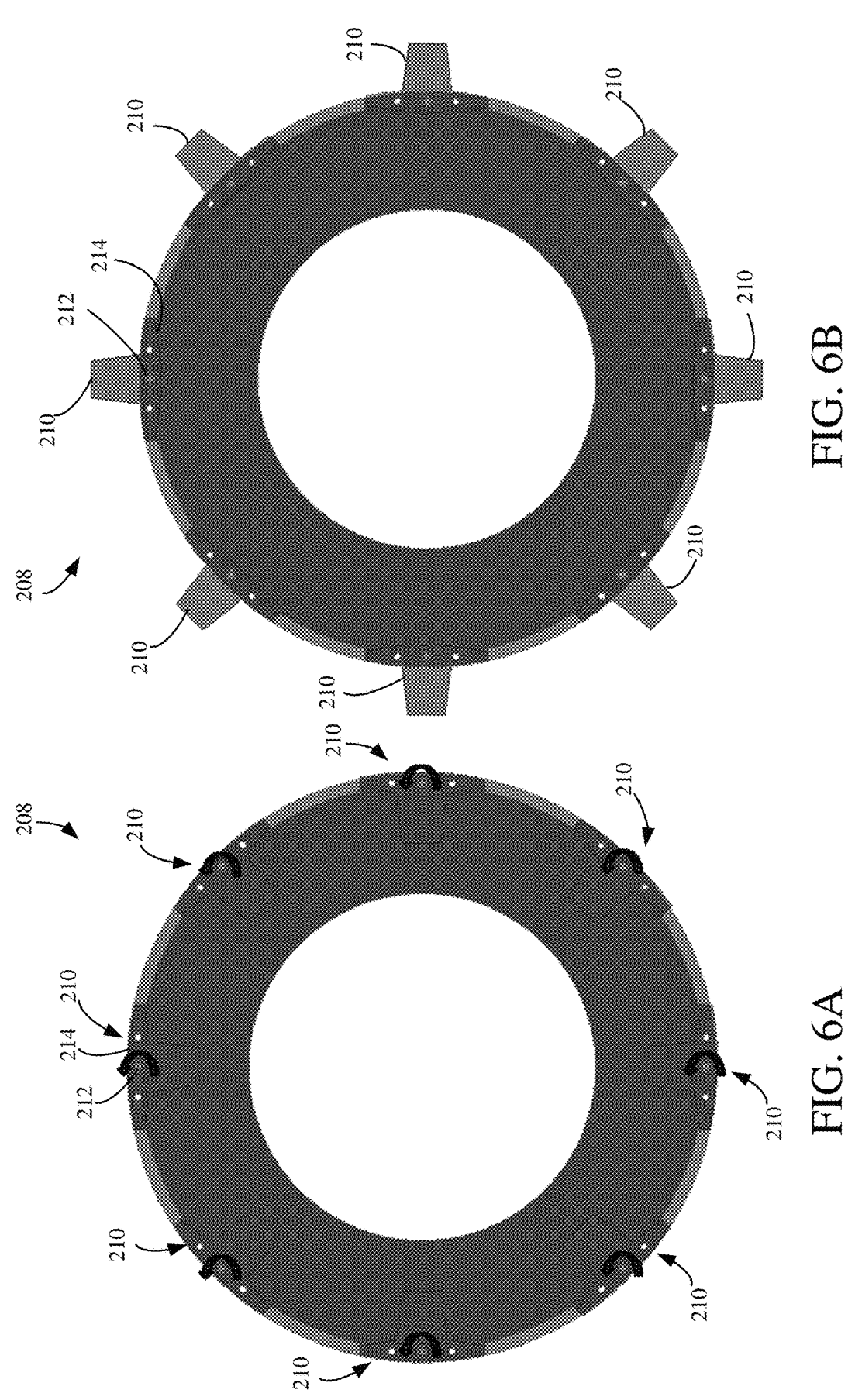
FIG. 6A and 6B show one example of a configurable closing system.

FIGS. 6A and 6B show another example of a configurable or adjustable closing wheel 208. Wheel 208 has a plurality of pivotable teeth 210 that can be pivoted about a pivot axis 212 from a first position shown in FIG. 6A to a second position shown in FIG. 6B. In the position shown in FIG. 6A, the teeth have a first surface 214 that forms part of a smooth soil engaging surface of wheel 208. When rotated to the position shown in FIG. 6B, the teeth 210 project outwardly relative to the surface of wheel 208 to provide a spiked, or more aggressive, soil engaging surface. In one example, the teeth 210 can be manually rotatable between the positions shown in FIGS. 6A and 6B and secured in the desired position using a cotter pin, a spring-loaded pin, or in another way. In another example, an actuator can be provided to automatically rotate each of the teeth between the positions shown in FIGS. 6A and 6B.

Figure 7:
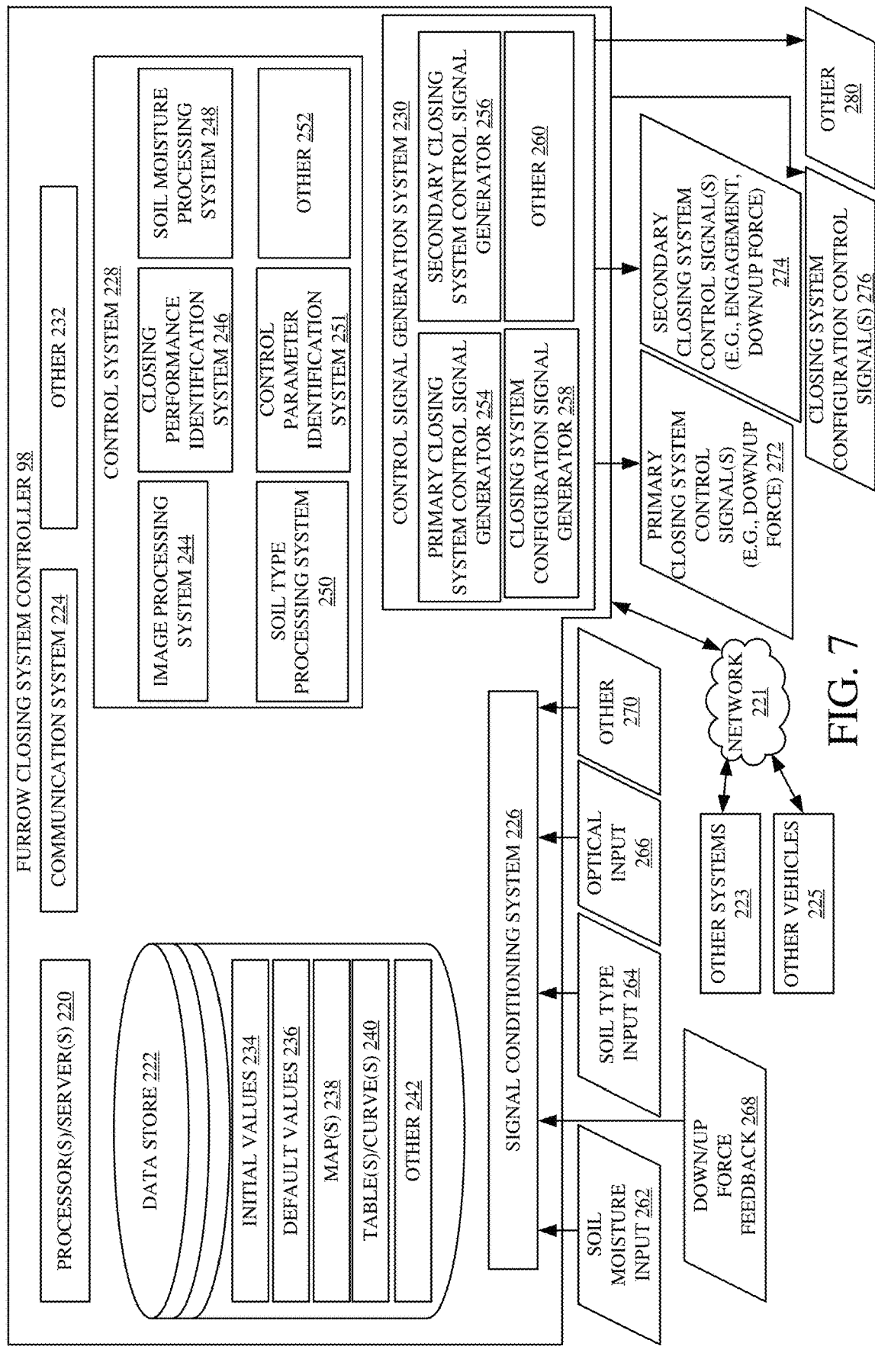
FIG. 7 is a block diagram of a furrow closing system controller.

FIG. 7 is a block diagram showing one example of furrow closing system controller 98 in more detail. FIG. 7 shows that controller 98 can communicate with other systems 223 and other vehicles 225 over network 221. Network 221 can be a wide area network, a local area network, a near field communication network, a cellular communication network, a Wi-Fi network, a Bluetooth network or any of a wide variety of other networks or combinations of networks. Other systems 223 can include farm manager systems, mapping systems, vendor systems, remote server systems (e.g., cloud-based systems), etc. Other vehicles 225 can include towing vehicle 94 or other vehicles. The other vehicles 225 can be vehicles operating in the same field as vehicle 94, vehicles that perform subsequent operations, or other vehicles. In the example shown in FIG. 7, furrow closing system controller 98 can include one or more processors or servers 220, data store 222, communication system 224, signal conditioning system 226, control system 228, control signal generation system 230, and other items 232. Data store 222 can include a plurality of initial values 234, default values 236, maps or mapped values 238, lookup tables or curves 240, and other items 242. Control system 228 can include image processing system 244, closing performance identification system 246, soil moisture processing system 248, soil type processing system 250, control parameter identification system 251, and other items 252. Control signal generation system 230 can include primary closing system control signal generator 254, secondary closing system control signal generator 256, closing system configuration signal generator 258, and other items 260. FIG. 7 also shows that furrow closing system controller 98 can include inputs from sensors, from maps, or from other systems, that include a soil moisture input 262, a soil type input 264, an optical input 266, a downforce/upforce feedback signal 268, and other items 270.

The soil moisture input 262 can be provided by soil moisture sensor 148 and indicate the soil moisture in the soil over which row unit 106 is traveling. The soil moisture input 262 can be received from a map of soil moisture inputs that is mapped to the geographic location over which row unit 106 is traveling in which case a position sensor, such as a global navigation satellite system-GNSS-receiver, an inertial measurement unit, a cellular triangulation system, a dead reckoning system, or another position system is used to sense the position of row unit 106 and generates an output indicative of that position. Soil type input 264 can also be provided from soil type sensor 150, or from a soil type mapping system that provides a soil type map, or another system that provides an input indicative of soil type. Furrow closing performance can be sensed based on optical input 266 which can be provided by image capture device 142 or another optical sensor. Down/upforce feedback input 268 can be provided by a sensor that senses the force 140 being applied to the furrow closing system by the ground (and thus being indicative of the downforce applied by one or more of the actuators 146 and 131. The down/upforce feedback input 268 can be provided by a sensor that senses the force applied by actuator 146 and 162, or by other sensors as well.

FIG. 7 also shows that control signal generation system 230 can generate a primary closing system control signal 272 that controls the primary closing system (such as closing wheels 124 and actuator 146). For instance, the primary closing system control signal 272 can control the amount of downforce or upforce exerted by actuator 146. Control signals 272 can include other control signals as well.

Control signal generation system 230 can also generate secondary closing system control signals 274. For instance, signals 274 can control actuator 162 to move secondary closing system 156 into and out of engagement with the ground and to exert a desired amount of downforce or upforce on the secondary closing system 156.

Control signal generation system 230 can also generate closing system configuration control signals 276. Signals 276 can control the configuration of the closing wheels. For instance, control signals 276 can control the rotation of hub 168 or hub 190, or the rotation of the teeth 210 illustrated in FIGS. 4A-6B, respectively, in order to change the configuration of the closing wheels to vary the aggressiveness with which the soil engaging surface of the closing wheels engages the soil.

Control signal generation system 238 can generate other control signals 280 as well.

Prior to describing the operation of furrow closing system controller 98 in more detail, a description of some of the items in furrow closing system controller 98, and their operation, will first be provided. Signal conditioning system 226 can perform signal conditioning on the inputs received, such as inputs from sensors or other systems. The signal conditioning can include such things as amplification, filtering, linearization, normalization, etc. The signals can then be provided to other items within furrow closing system controller 98.

Communication system 224 can be used to communicate over network 221 with other systems 223 and/or other vehicles 225. Therefore, communication system 224 can be configured based upon the type of network 221. In addition, communication system 224 can facilitate communication of the items of furrow closing system controller 98 among themselves. Therefore, communication system 224 can include a controller area network (CAN) bus and bus controller, and/or other items that are used to facilitate communication.

Image processing system 244 can receive the optical input 266 and perform image processing to identify characteristics of images captured by image capture device 142. For instance, image processing system 244 can identify the furrow, the state of whether the furrow has opened or closed, seeds, seed location, or other items in the image. Closing performance identification system 246 can then generate an output indicative of the closing performance of the furrow closing system that is currently engaged in closing the furrow. For instance, if the furrow is consistently closed and indicates that there is good seed-to-soil contact or seed-to-moisture contact, then system 246 may generate an output to indicate a relatively high closing performance. However, if the furrow is sporadically or continuously open or otherwise indicates that there is not good seed-to-soil contact, or seed-to-moisture contact then the closing performance identification system 246 generates an output indicating that the closing performance is relatively poor. The output can be provided to control parameter identification system 251 for identification of the furrow closing system control parameters.

Soil moisture processing system 248 receives the soil moisture input 262 and generates an output indicative of how the closing system should be controlled based on soil moisture. For instance, soil moisture processing system 248 can process a soil moisture input 262 to identify the soil moisture and system 251 can access tables/curves 240 which identify, based upon the soil moisture, what the closing system configuration, downforce/upforce, aggressiveness of engagement, etc. should be. System 251 can then generate an output indicative of those control parameters.

Soil type processing system 250 can receive the soil type input 264 indicative of soil type. Soil type processing system 250 can be a map processing system that processes a soil type map input or a sensor processing system that processes a soil type sensor input or another system. Based upon the soil type, system 251 also accesses information in data store 222 or executes an algorithm or otherwise generates an output indicative of the control parameters for controlling the furrow closing system based upon the soil type.

It should also be noted that control system 228 can generate an output based upon a plurality of the different sensed values or a plurality of inputs (such as one or more of soil moisture, soil type, closing performance, etc.). By way of example, if the soil type is clay and the moisture content is high, this may mean that one set of closing control parameters should be used. However, if the soil moisture is high but the soil type is sand, then this may mean that a different set of closing control parameters should be used.

Therefore, control parameter identification system 251 can generate the output based on one or more of the outputs from systems 244, 246, 248, 250, and 252. System 251 can perform calculations or use models or machine learned systems to identify the closing control parameters based upon the various inputs. System 251 can also access tables or curves 240, maps 238, and other information in data store 222 or elsewhere, in order to identify the control parameters.

Control signal generation system 230 receives the outputs from control system 228 indicative of the control parameters, and generates control signals 272-280 based upon the identified control parameters. Primary closing system control signal generator 254 generates control signals to control the primary closing system (e.g., closing wheels 124 and actuator 146, etc.) while secondary closing system control signal generator 256 generates control signals to control the secondary closing system 156 (where one is present) based upon the identified control parameters. It will be noted that, while the present discussion proceeds with respect to a secondary closing system 156, there can be any number of additional closing systems controlled as well. The present discussion is provided by way of example only. Closing system configuration signal generator 258 generates control signals 276 to control the configuration of configurable or adjustable closing wheels (such as those shown in FIGS. 4A-6B). System 230 can generate other control signals 280 as well.

Figure 8:
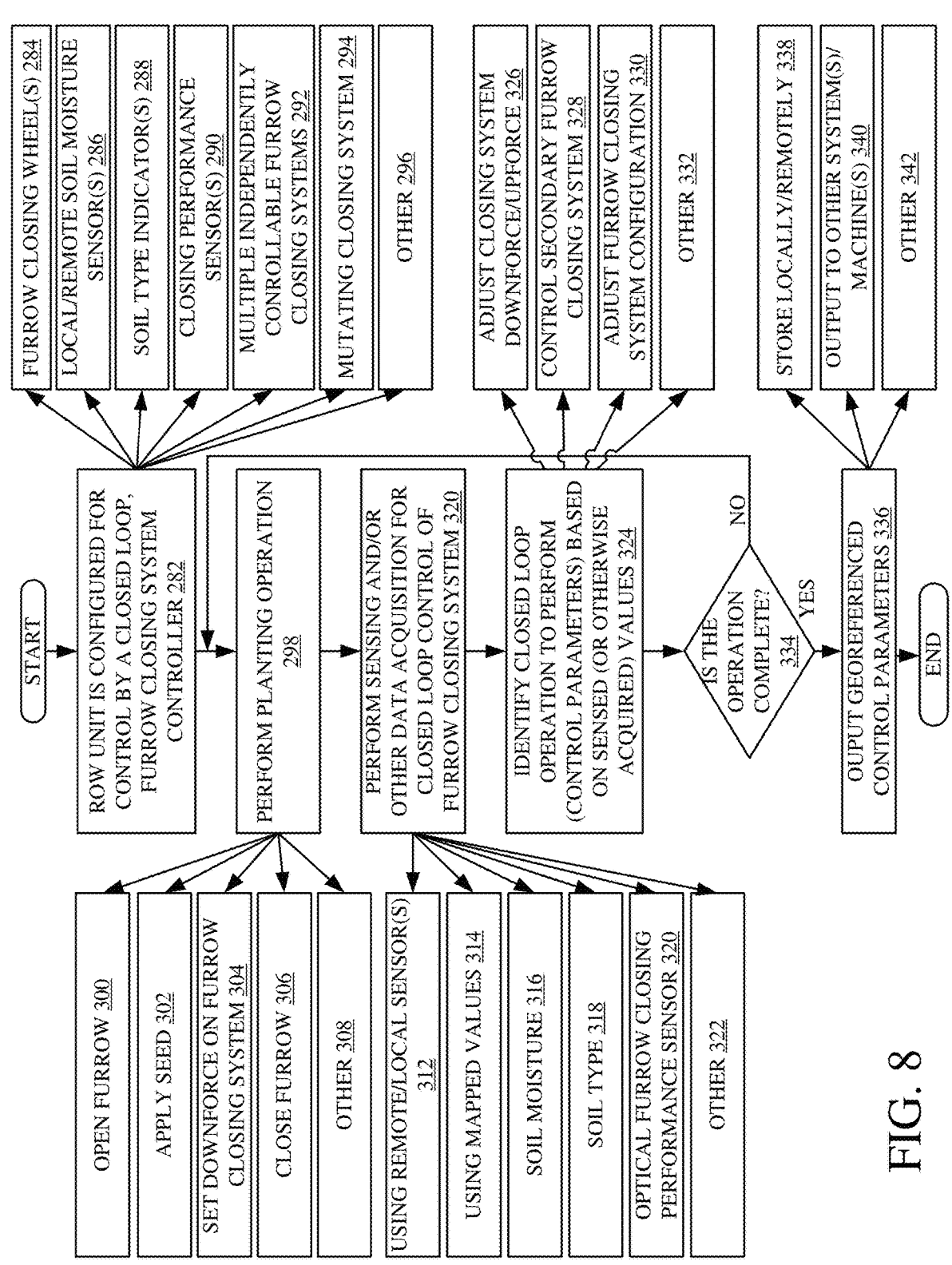
FIG. 8 is a flow diagram showing one example of the operation of an agricultural machine.

FIG. 8 is a flow diagram illustrating one example of the operation of a row unit 106 and furrow closing system controller 98.

It is first assumed that a row unit 106 is configured for control by a closed loop furrow closing system controller (such as controller 98 shown in FIG. 7). Having a row unit 106 configured in this way is indicated by block 282 in the flow diagram of FIG. 8. In one example, the furrow closing system on the row unit includes furrow closing wheels 284 but can be any other type of furrow closing system such as one or more disc closers, a chain harrow, single or multiple closing blades, one or more plate closers, etc. The furrow closing system controller 98 can receive an input from a local or remote soil moisture sensor, or another soil moisture indicator, as indicated by block 286. The furrow closing system controller 98 can receive an input indicative of soil type, as indicated by block 288, and/or an input from one or more closing performance sensors such as optical sensors (e.g., image capture device 142) as indicated by block 290 in the flow diagram of FIG. 8. In another example, the row unit can have multiple, independently controllable furrow closing systems, as indicated by block 292, such as furrow closing wheels 124 with actuator 146, and secondary furrow closing system 156. Also, in one example, the row unit 106 can have a mutating or adjustable closing system 294 which can be controlled to change the aggressiveness of the soil engaging surface of the closing system. Examples of this are discussed above with respect to FIGS. 4A-6B. The row unit can be configured for control by a closed loop, furrow closing system controller in other ways as well, as indicated by block 296 in the flow diagram of FIG. 8.

Row unit 106 is then controlled to begin performing a planting operation, as indicated by block 298 in the flow diagram of FIG. 8. The furrow openers 120 open a furrow, as indicated by block 300. Seed is applied to the furrow as indicated by block 302. A closing system downforce is set by actuating actuator 146 on the furrow closing system, as indicated by block 304 in the flow diagram of FIG. 8, and the furrow is closed by the furrow closing system (e.g., closing wheels 124) as indicated by block 306 in the flow diagram of FIG. 8. The planting operation can be performed in other ways as well, as indicated by block 308.

The furrow closing system controller 98 then receives inputs from sensing and/or other data acquisition systems to obtain information for performing closed loop control of the furrow closing system. Performing sensing or obtaining information in other ways to perform closed loop control is indicated by block 310 in the flow diagram of FIG. 8. Furrow closing system controller 98 can obtain information from remote or local sensors, as indicated by block 312, or using mapped values, as indicated by block 314. The information obtained and used for closed loop control can be soil moisture 316, soil type 318, optical furrow closing performance information 320, and/or any of a wide variety of other information 322. The control system 228 then identifies closed loop operations to perform (e.g., control parameters) based upon the sensed or otherwise acquired values, as indicated by block 324 in the flow diagram of FIG. 8.

The control parameters that are identified can identify an adjustment that should be made to the closing system downforce or upforce, as indicated by block 326 in the flow diagram of FIG. 8. The control parameters can indicate how to control the secondary furrow closing system, such as whether to control it to engage the soil, the aggressiveness of engagement, the downforce or upforce used during engagement, etc., as indicated by block 328 in the flow diagram of FIG. 8. The control parameters can indicate that the configuration of the furrow closing system should be adjusted (such as to obtain a more aggressive soil engaging surface, or a less aggressive soil engaging surface, etc.), as indicated by block 330. The control parameter can also identify where adjustments or other actions were performed or are to be performed. Position parameters can thus be included as well. The parameters can identify alerts or fault codes based on the sensed information. Such alerts or fault codes can indicate that the furrow is not being adequately closed, that seeds are not in the furrow, or any of the wide variety of other parameters indicative of improper performance.

It will noted that either or both of the primary and secondary closing systems can be configurable or adjustable as well. Therefore, for instance, one may be adjusted to obtain a more aggressive soil engaging surface while the other is adjusted to obtain a less aggressive soil engaging surface. These are examples only. A wide variety of other control parameters can be identified as well in order to perform closed loop control of the furrow closing system, as indicated by block 332 in the flow diagram of FIG. 8.

Until the operation is complete, as indicated by block 334, processing reverts to block 298 where the planting operation continues and the closed loop control of the furrow closing system also continues.

Once the operation is complete, or during the operation, control system 228 can also control communication system 224 to output georeferenced control parameters (control parameters georeferenced to a location in the field where they were employed) to different systems, as indicated by block 336. For instance, the georeferenced control parameters can be stored locally on data store 222 or remotely on another system 223, as indicated by block 338. The georeferenced control parameters can be output to other systems 223 or vehicles or machines 225, as indicated by block 340. The georeferenced control parameters can be output or saved in other ways as well, or output to other systems, as indicated by block 342.

It can thus be seen that the present description describes a system which employs closed loop control of the furrow closing system on a row unit. The closed loop control can be performed based upon soil moisture, soil type, furrow closing performance, or other sensed or received or obtained criteria. The closed loop control can identify control parameters such as controlling the downforce or upforce on a closing system, whether to deploy a secondary closing system and the downforce or upforce on that system, the configuration of the closing system (such as the aggressiveness of the soil engaging surface of the closing system), and other control parameters. The control parameters can be identified and executed automatically to save time and effort on the part of the operator. This can also increase the speed with which the planting operation is performed, the accuracy and efficiency of the planting operation, among other things. By automatically it is meant, in one example, that the function or operation is performed without further human involvement except, perhaps, to initiate or authorize the function or process.

It will be noted that the above discussion has described a variety of different systems, components, processors, generators, and/or logic. It will be appreciated that such systems, components, processors, generators, and/or logic can be comprised of hardware items (such as processors and associated memory, or other processing components, some of which are described below) that perform the functions associated with those systems, components, processors, generators, and/or logic. In addition, the systems, components and/or logic can be comprised of software that is loaded into a memory and is subsequently executed by a processor or server, or other computing component, as described below. The systems, components, processors, generators, and/or logic can also be comprised of different combinations of hardware, software, firmware, etc., some examples of which are described below. These are only some examples of different structures that can be used to form the systems, components, processors, generators, and/or logic described above. Other structures can be used as well.

The present discussion has mentioned processors, processing systems, controllers and/or servers. In one example, these can include computer processors with associated memory and timing circuitry, not separately shown. They are functional parts of the systems or devices to which they belong and are activated by, and facilitate the functionality of the other components or items in those systems.

Also, a number of user interface (UI) displays have been discussed. The UI displays can take a wide variety of different forms and can have a wide variety of different user actuatable input mechanisms disposed thereon. For instance, the user actuatable input mechanisms can be text boxes, check boxes, icons, links, drop-down menus, search boxes, etc. The mechanisms can also be actuated in a wide variety of different ways. For instance, the mechanisms can be actuated using a point and click device (such as a track ball or mouse). The mechanisms can be actuated using hardware buttons, switches, a joystick or keyboard, thumb switches or thumb pads, etc. The mechanisms can also be actuated using a virtual keyboard or other virtual actuators. In addition, where the screen on which they are displayed is a touch sensitive screen, the mechanisms can be actuated using touch gestures. Also, where the device that displays them has speech recognition components, the mechanisms can be actuated using speech commands.

A number of data stores have also been discussed. It will be noted the data stores can each be broken into multiple data stores. All can be local to the systems accessing them, all can be remote, or some can be local while others are remote. All of these configurations are contemplated herein.

Also, the figures show a number of blocks with functionality ascribed to each block. It will be noted that fewer blocks can be used so the functionality is performed by fewer components. Also, more blocks can be used with the functionality distributed among more components.

Figure 9:
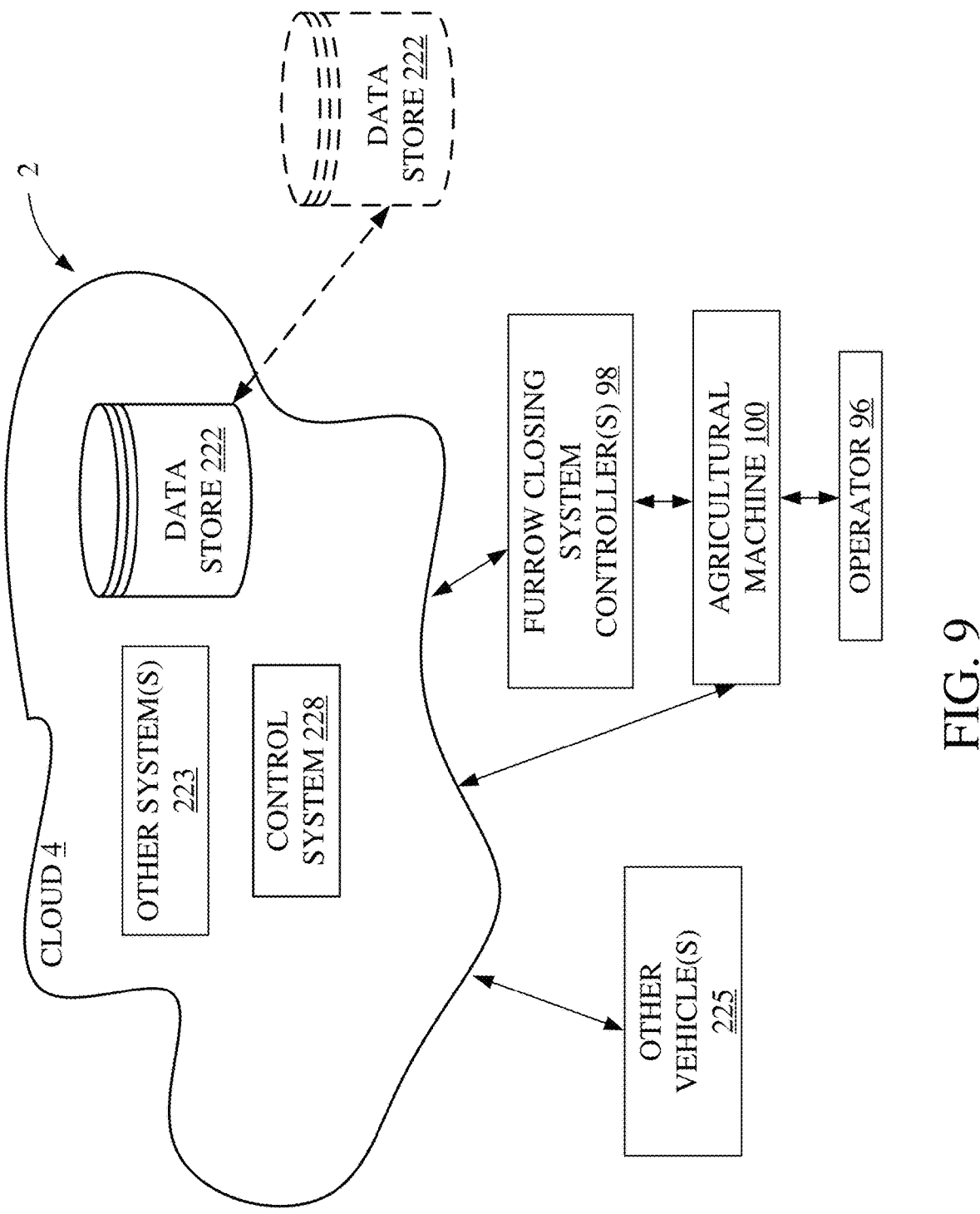
FIG. 9 is a block diagram showing one example of the items illustrated in FIGS. 1-7, deployed in a remote server architecture.

FIG. 9 is a block diagram of one example of the agricultural machine architecture, shown in FIGS. 1-7, where system 98 communicates with elements in a remote server architecture 2. In an example, remote server architecture 2 can provide computation, software, data access, and storage services that do not require end-user knowledge of the physical location or configuration of the system that delivers the services. In various examples, remote servers can deliver the services over a wide area network, such as the internet, using appropriate protocols. For instance, remote servers can deliver applications over a wide area network and they can be accessed through a web browser or any other computing component. Software or components shown or described in FIGS. 1-7 as well as the corresponding data, can be stored on servers at a remote location. The computing resources in a remote server environment can be consolidated at a remote data center location or they can be dispersed. Remote server infrastructures can deliver services through shared data centers, even though they appear as a single point of access for the user. Thus, the components and functions described herein can be provided from a remote server at a remote location using a remote server architecture. Alternatively, they can be provided from a conventional server, or they can be installed on client devices directly, or in other ways.

In the example shown in FIG. 9, some items are similar to those shown in FIGS. 1-7 and they are similarly numbered. FIG. 9 specifically shows that control system 228, and other systems 223 can be located at a remote server location 4. Therefore, system 98 accesses those systems through remote server location 4.

Regardless of where they are located, the items can be accessed directly by system 98, through a network (either a wide area network or a local area network), they can be hosted at a remote site by a service, or they can be provided as a service, or accessed by a connection service that resides in a remote location. Also, the data can be stored in substantially any location and intermittently accessed by, or forwarded to, interested parties. For instance, physical carriers can be used instead of, or in addition to, electromagnetic wave carriers. In such an example, where cell coverage is poor or nonexistent, another mobile machine (such as a fuel truck) can have an automated information collection system. As the agricultural machine comes close to the fuel truck for fueling, the system automatically collects the information from the machine or transfers information to the machine using any type of ad-hoc wireless connection. The collected information can then be forwarded to the main network as the fuel truck reaches a location where there is cellular coverage (or other wireless coverage). For instance, the fuel truck may enter a covered location when traveling to fuel other machines or when at a main fuel storage location. All of these architectures are contemplated herein. Further, the information can be stored on the agricultural machine until the agricultural machine enters a covered location. The agricultural machine, itself, can then send and receive the information to/from the main network.

It will also be noted that the elements of FIGS. 1-7, or portions of them, can be disposed on a wide variety of different devices. Some of those devices include servers, desktop computers, laptop computers, tablet computers, or other mobile devices, such as palm top computers, cell phones, smart phones, multimedia players, personal digital assistants, etc.

Figure 10:
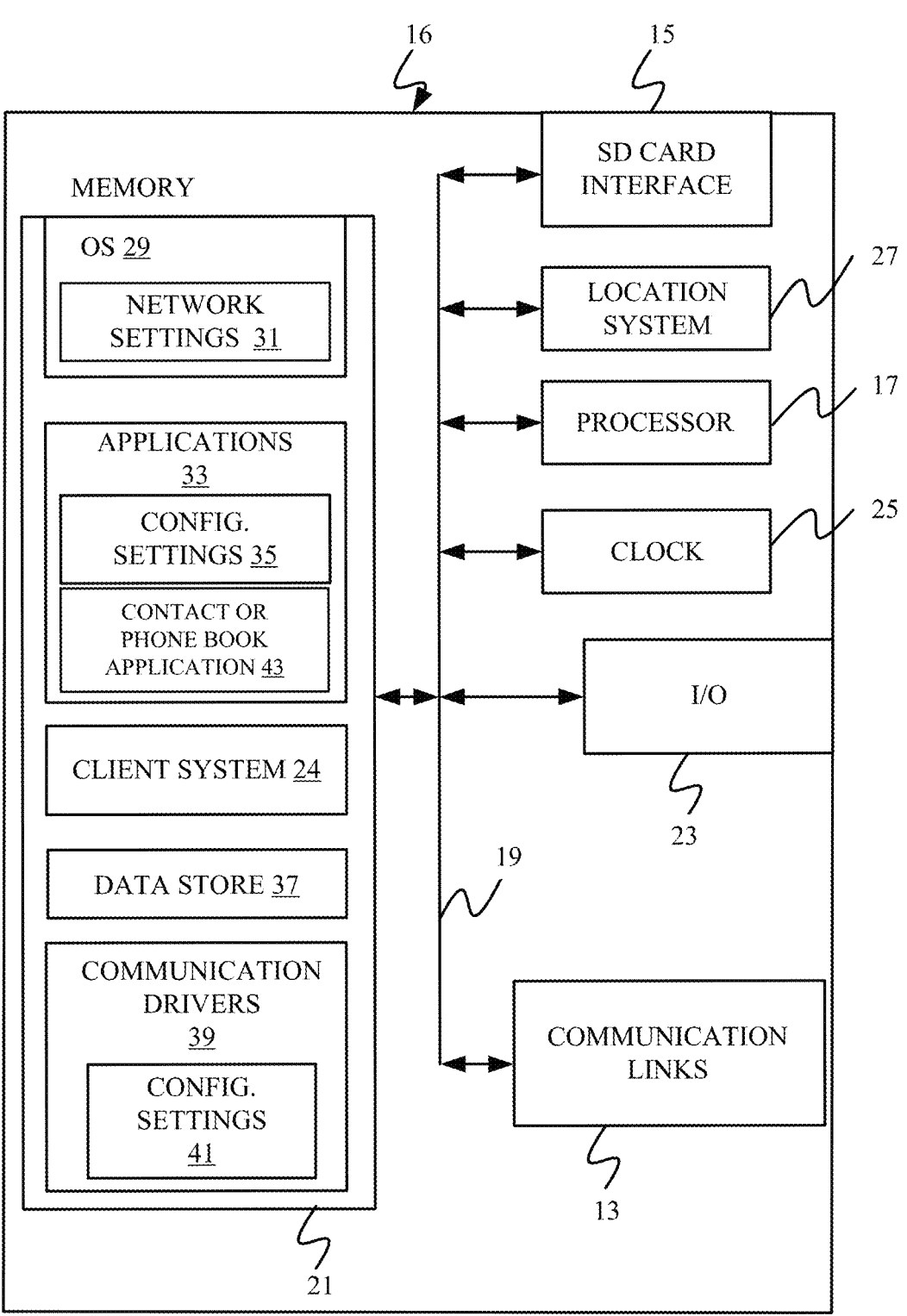
FIGS. 10-12 show examples of mobile devices that can be used in other systems or architectures.
Figure 11:
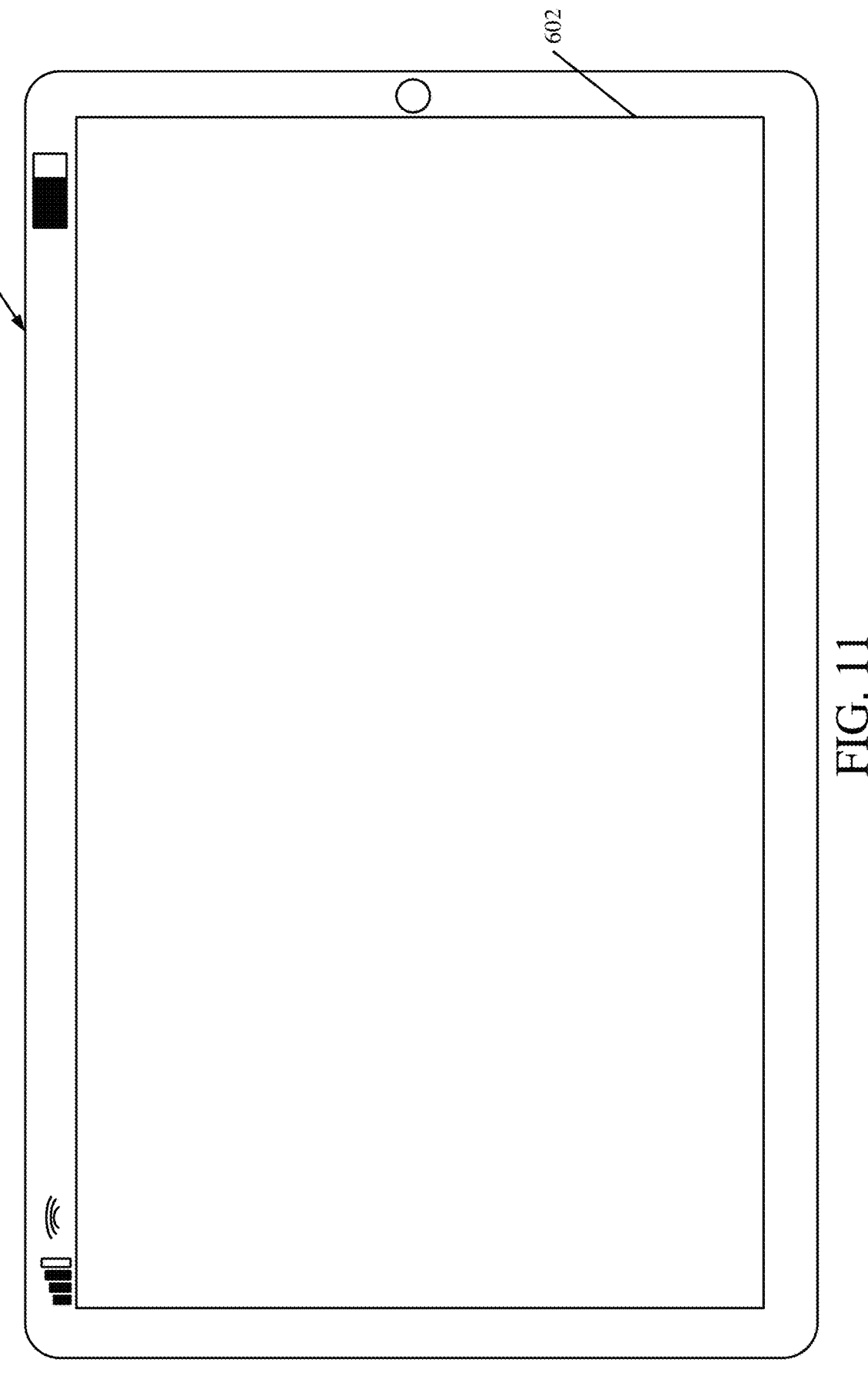
Figure 12:
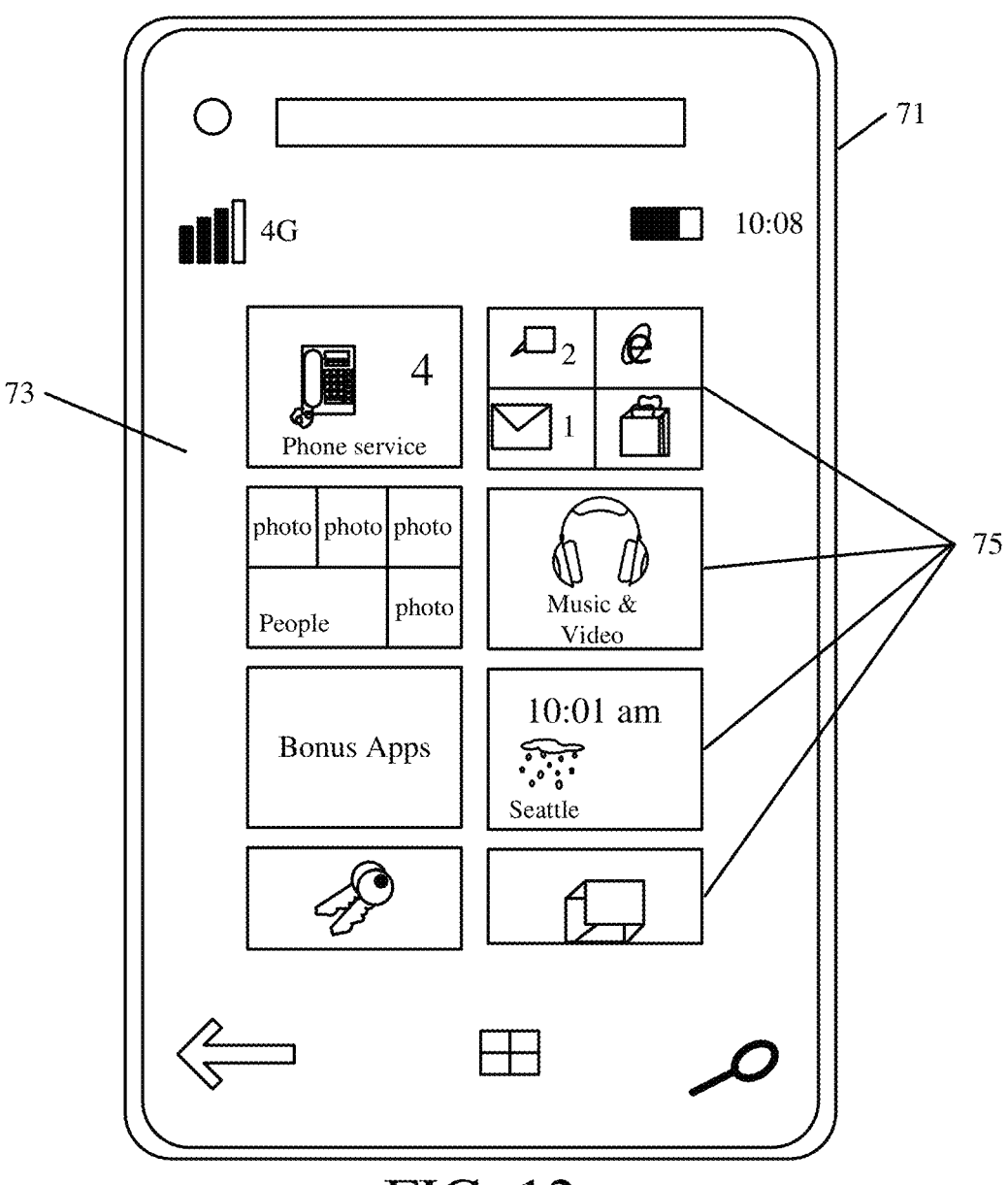
Figure 13:
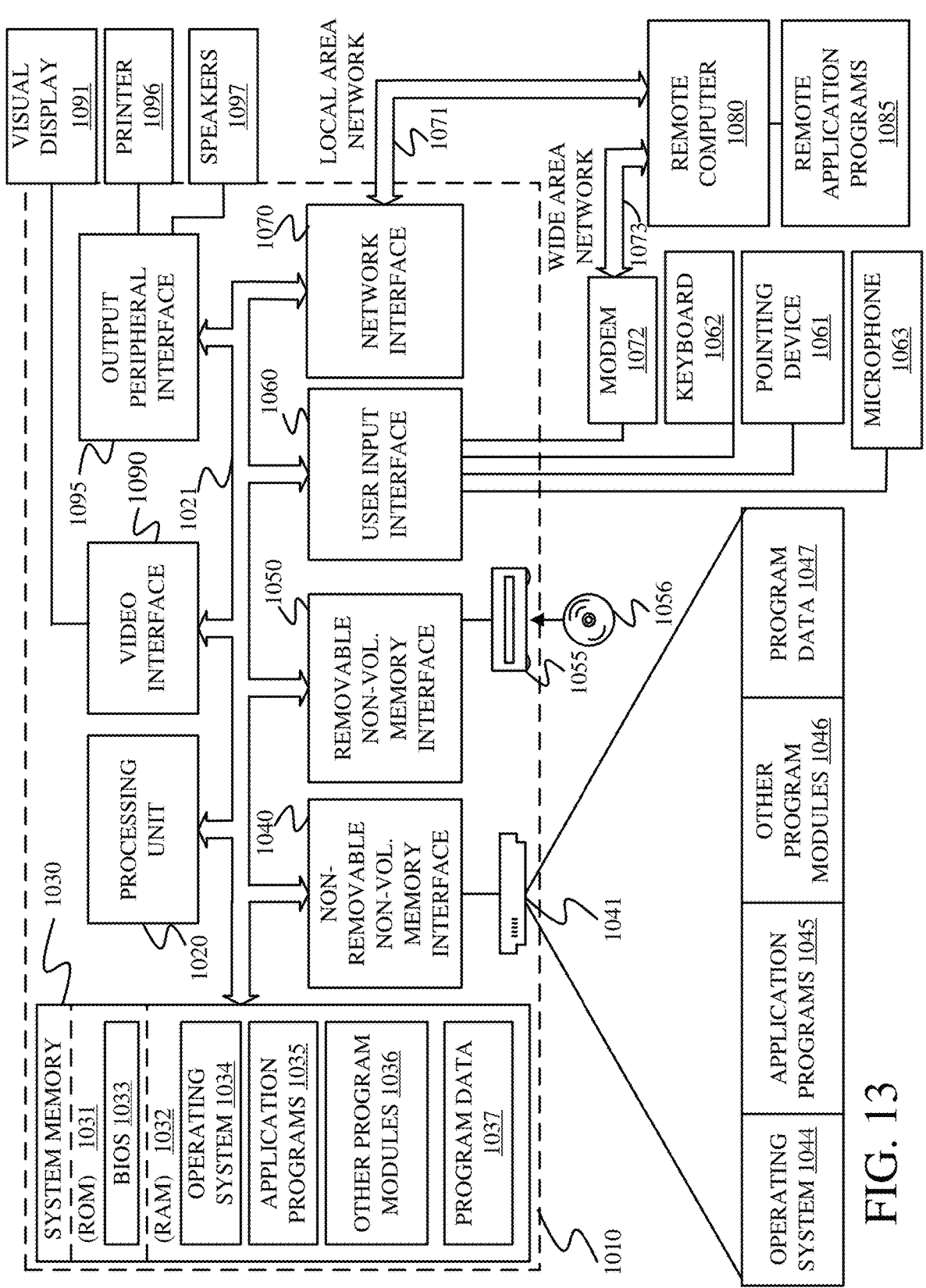
FIG. 13 is a block diagram showing one example of a computing environment that can be used in the architectures or systems shown in the previous figures.

FIG. 10 is one example of a computing environment in which elements of FIGS. 1-7, or parts of it, (for example) can be deployed. With reference to FIG. 10, an example system for implementing some embodiments includes a computing device in the form of a computer 1010. Components of computer 1010 may include, but are not limited to, a processing unit 1020 (which can comprise processors or servers from previous FIGS.), a system memory 1030, and a system bus 1021 that couples various system components including the system memory to the processing unit 1020. The system bus 1021 may be any of several types of bus structures including a memory bus or memory controller, a peripheral bus, and a local bus using any of a variety of bus architectures. Memory and programs described with respect to FIGS. 1-7 can be deployed in corresponding portions of FIG. 10.

Computer 1010 typically includes a variety of computer readable media. Computer readable media can be any available media that can be accessed by computer 1010 and includes both volatile and nonvolatile media, removable and non-removable media. By way of example, and not limitation, computer readable media may comprise computer storage media and communication media. Computer storage media is different from, and does not include, a modulated data signal or carrier wave. It includes hardware storage media including both volatile and nonvolatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by computer 1010. Communication media may embody computer readable instructions, data structures, program modules or other data in a transport mechanism and includes any information delivery media. The term "modulated data signal" means a signal that has one or more of its characteristics set or changed in such a manner as to encode information in the signal.

The system memory 1030 includes computer storage media in the form of volatile and/or nonvolatile memory such as read only memory (ROM) 1031 and random access memory (RAM) 1032. A basic input/output system 1033 (BIOS), containing the basic routines that help to transfer information between elements within computer 1010, such as during start-up, is typically stored in ROM 1031. RAM 1032 typically contains data and/or program modules that are immediately accessible to and/or presently being operated on by processing unit 1020. By way of example, and not limitation, FIG. 10 illustrates operating system 1034, application programs 1035, other program modules 1036, and program data 1037.

The computer 1010 may also include other removable/non-removable volatile/nonvolatile computer storage media. By way of example only, FIG. 10 illustrates a hard disk drive 1041 that reads from or writes to non-removable, nonvolatile magnetic media, an optical disk drive 1055, and nonvolatile optical disk 1056. The hard disk drive 1041 is typically connected to the system bus 1021 through a non-removable memory interface such as interface 1040, and optical disk drive 1055 is typically connected to the system bus 1021 by a removable memory interface, such as interface 1050.

Alternatively, or in addition, the functionality described herein can be performed, at least in part, by one or more hardware logic components. For example, and without limitation, illustrative types of hardware logic components that can be used include Field-programmable Gate Arrays (FPGAs), Application-specific Integrated Circuits (e.g., ASICs), Application-specific Standard Products (e.g., ASSPs), System-on-a-chip systems (SOCs), Complex Programmable Logic Devices (CPLDs), etc.

The drives and their associated computer storage media discussed above and illustrated in FIG. 10, provide storage of computer readable instructions, data structures, program modules and other data for the computer 1010. In FIG. 10, for example, hard disk drive 1041 is illustrated as storing operating system 1044, application programs 1045, other program modules 1046, and program data 1047. Note that these components can either be the same as or different from operating system 1034, application programs 1035, other program modules 1036, and program data 1037.

A user may enter commands and information into the computer 1010 through input devices such as a keyboard 1062, a microphone 1063, and a pointing device 1061, such as a mouse, trackball or touch pad. Other input devices (not shown) may include a joystick, game pad, satellite dish, scanner, or the like. These and other input devices are often connected to the processing unit 1020 through a user input interface 1060 that is coupled to the system bus, but may be connected by other interface and bus structures. A visual display 1091 or other type of display device is also connected to the system bus 1021 via an interface, such as a video interface 1090. In addition to the monitor, computers may also include other peripheral output devices such as speakers 1097 and printer 1096, which may be connected through an output peripheral interface 1095.

The computer 1010 is operated in a networked environment using logical connections (such as a local area network-LAN, or wide area network-WAN, or a controller area network-CAN) to one or more remote computers, such as a remote computer 1080.

When used in a LAN networking environment, the computer 1010 is connected to the LAN 1071 through a network interface or adapter 1070. When used in a WAN networking environment, the computer 1010 typically includes a modem 1072 or other means for establishing communications over the WAN 1073, such as the Internet. In a networked environment, program modules may be stored in a remote memory storage device. FIG. 10 illustrates, for example, that remote application programs 1085 can reside on remote computer 1080.

It should also be noted that the different examples described herein can be combined in different ways. That is, parts of one or more examples can be combined with parts of one or more other examples. All of this is contemplated herein.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. An agricultural machine, comprising:
a furrow opener opening a furrow in soil;

planting functionality providing seed to the furrow;
a furrow closing system that engages the soil to close the furrow, the furrow closing system comprising:
a primary furrow closing system; and
a secondary furrow closing system;
a soil sensor sensing a characteristic indicative of a closing performance of the primary furrow closing system in moving the soil to close the furrow and generating a soil sensor signal representing the closing performance of the primary furrow closing system; and
a furrow closing system controller that receives the soil sensor signal representing the closing performance of the primary furrow closing system and that generates a closing system control signal to control the secondary furrow closing system based on the soil sensor signal representing the closing performance of the primary furrow closing system.

2. The agricultural machine of claim 1 wherein the primary furrow closing system comprises:
a closer; and
an actuator coupled to the closer to exert a downforce on the closer, the furrow closing system controlling the actuator based on the soil sensor signal.

3. The agricultural machine of claim 2 comprising:
a moisture sensor that senses soil moisture, wherein the furrow closing system is controlled based on the soil moisture.

4. The agricultural machine of claim 2 comprising:
a soil type sensor that senses soil type, wherein the furrow closing system is controlled based on the soil type.

5. The agricultural machine of claim 4 wherein the soil type sensor comprises;
a map processing system that receives a soil type map and that processes the soil type map to obtain soil type.

6. The agricultural machine of claim 1 wherein the soil sensor comprises an image capture device that captures an image of the soil after the primary furrow closing system has traveled over the soil, and further comprising:
an image processor that identifies the closing performance of the primary furrow closing system based on the image.

7. The agricultural machine of claim 6 wherein the image capture device comprises a stereo camera.

8. The agricultural machine of claim 1 wherein the secondary furrow closing system comprises:
a closer; and
an actuator that moves the closer between a first position in engagement with the soil and a second position out of engagement with the soil and wherein the furrow closing system controller generates the closing system control signal to move the closer between the first position and the second position.

9. The agricultural machine of claim 1 wherein one of the primary furrow closing system or the secondary furrow closing system comprises:
a closer with a soil engaging surface that is controllably adjustable to change a shape of the soil engaging surface of the closer, the furrow closing system controller generating the closing system control signal to control the shape of the soil engaging surface of the closer based on the soil sensor signal.

10. The agricultural machine of claim 1, wherein the primary furrow closing system has a first soil engaging surface and wherein the secondary furrow closing system has a second soil engaging surface, different than the first soil engaging surface.

11. The agricultural machine of claim 10, wherein the first soil engaging surface is smooth and the second soil engaging surface is non-smooth.

12. A control system on an agricultural machine, the control system comprising:

a controller that receives a soil sensor signal indicative of a closing performance of a primary furrow closing system in moving soil to close a furrow and identifies, responsive to the soil sensor signal indicative of the closing performance of the primary furrow closing system, a control parameter for controlling a secondary furrow closing system; and a control signal generator that generates a closing system control signal to control downforce applied by the secondary furrow closing system to the soil based on the control parameter.

13. The control system of claim 12 wherein the controller receives a soil moisture characteristic and identifies the control parameter based on the soil moisture characteristic, the controller and the control signal generator performing closed loop control of the downforce applied by at least one of the primary furrow closing system or secondary furrow closing system based on the soil moisture characteristic.

14. The control system of claim 12 wherein the secondary furrow closing system comprises a closer and an actuator that moves the closer between a first position in engagement with the soil and a second position out of engagement with the soil and wherein the controller identifies, as the control parameter, a position to which to move the closer.

15. The control system of claim 12 wherein at least one of the primary furrow closing system or the secondary furrow closing system comprises an adjustable closer with a soil engaging surface that is controllable to change a shape of the soil engaging surface of the adjustable closer, the controller identifying, as the control parameter, the shape of the soil engaging surface of the adjustable closer based on the soil sensor signal.

16. A method of controlling an agricultural machine, comprising:

opening a furrow in soil;

providing seed to the furrow;

engaging the soil to close the furrow with a primary furrow closing system;

sensing a characteristic of the soil after the primary furrow closing system has engaged the soil, wherein the characteristic comprises a closing performance of the primary furrow closing system generating a soil sensor signal representing the closing performance of the primary furrow closing system and generating a control signal to selectively engage or disengage a secondary furrow closing system with the soil based on the soil sensor signal representing the closing performance of the primary furrow closing system.

17. The method of claim 16 wherein the control signal controls a downforce applied by the secondary furrow closing system to the soil.

18. The method of claim 16, wherein the characteristic comprising soil moisture.

19. The method of claim 16, wherein the characteristic comprising soil type.

* * * * *